United States Patent
Sorg et al.

(10) Patent No.: US 9,291,315 B2
(45) Date of Patent: Mar. 22, 2016

(54) LIGHTING DEVICE

(71) Applicant: OSRAM GmbH, Munich (DE)

(72) Inventors: Joerg Sorg, Regensburg (DE); Florian Boesl, Regensburg (DE); Dennis Sprenger, Roethenbach a.d. Pegnitz (DE)

(73) Assignee: OSRAM GmbH, Munich (DE)

( * ) Notice: Subject to any disclaimer, the term of this patent is extended or adjusted under 35 U.S.C. 154(b) by 0 days.

(21) Appl. No.: 14/320,669

(22) Filed: Jul. 1, 2014

(65) Prior Publication Data

US 2015/0062955 A1 Mar. 5, 2015

(30) Foreign Application Priority Data

Aug. 30, 2013 (DE) .......................... 10 2013 217 319

(51) Int. Cl.
- *F21V 9/16* (2006.01)
- *F21V 7/04* (2006.01)
- *G01S 1/00* (2006.01)
- *G09B 9/00* (2006.01)
- *H01S 3/00* (2006.01)
- *H01S 3/30* (2006.01)

(Continued)

(52) U.S. Cl.
CPC ................ *F21K 9/56* (2013.01); *A61B 1/0653* (2013.01); *A61B 1/07* (2013.01); *F21K 9/52* (2013.01); *F21S 48/1145* (2013.01); *F21S 48/1225* (2013.01); *F21S 48/214* (2013.01); *F21V 9/16* (2013.01); *G02B 6/00* (2013.01); *G03B 21/204* (2013.01); *G03B 21/208* (2013.01); *A61B 1/05* (2013.01); *F21Y 2101/025* (2013.01)

(58) Field of Classification Search
CPC ............... F21K 9/56; F21K 9/52; F21V 9/16; F21S 48/1225
USPC ..................................................... 362/553, 84
See application file for complete search history.

(56) References Cited

U.S. PATENT DOCUMENTS 6,767,111 B1 * 7/2004 Lai .......................... F21V 5/008
  362/240
7,612,383 B2 * 11/2009 Andrews ................ H01L 33/58
  257/436

(Continued)

FOREIGN PATENT DOCUMENTS

DE     202012005157 U1    8/2012
EP         1921477 A2     5/2008

OTHER PUBLICATIONS

Search Report issued in the corresponding German application No. 102013217319.9, dated Mar. 21, 2014.

*Primary Examiner* — Robert May
*Assistant Examiner* — Bryon T Gyllstrom
(74) *Attorney, Agent, or Firm* — Viering, Jentschura & Partner MBB

(57) ABSTRACT

In various embodiments, a lighting device includes at least one laser light source and a light wavelength conversion element. The light wavelength conversion element includes phosphor which is arranged on a surface region of a substrate and is used for wavelength conversion of the light emitted by the at least one laser light source. The light wavelength conversion element has a greater thickness at the edge of the surface region, provided with phosphor, of the substrate than at the surface centroid of the surface region, provided with phosphor, of the substrate. The thickness is respectively measured perpendicularly to the surface region, provided with phosphor, of the substrate.

5 Claims, 5 Drawing Sheets

(51) Int. Cl.
*F21K 99/00* (2010.01)
*F21S 8/10* (2006.01)
*G02B 6/00* (2006.01)
*G03B 21/20* (2006.01)
*A61B 1/06* (2006.01)
*A61B 1/07* (2006.01)
*A61B 1/05* (2006.01)
*F21Y 101/02* (2006.01)

(56) References Cited

U.S. PATENT DOCUMENTS

| | | | |
|---|---|---|---|
| 8,262,251 B2* | 9/2012 | Rains, Jr. | B82Y 30/00 362/231 |
| 2003/0038291 A1* | 2/2003 | Cao | F21K 9/135 257/81 |
| 2003/0039122 A1* | 2/2003 | Cao | F21K 9/135 362/294 |
| 2006/0164833 A1* | 7/2006 | Parkyn | F21S 4/008 362/235 |
| 2008/0106887 A1* | 5/2008 | Salsbury | F21K 9/56 362/84 |
| 2010/0033948 A1* | 2/2010 | Harbers | F21K 9/54 362/84 |
| 2010/0061078 A1* | 3/2010 | Kim | H01L 33/50 362/84 |
| 2010/0085631 A1 | 4/2010 | Kusukame et al. | |
| 2012/0300431 A1* | 11/2012 | You | H01L 25/0753 362/84 |
| 2013/0093313 A1* | 4/2013 | Oyamada | H01L 33/505 313/503 |
| 2015/0211708 A1* | 7/2015 | Stavely | F21V 5/007 348/164 |

* cited by examiner

LIGHTING DEVICE

CROSS-REFERENCE TO RELATED APPLICATION

This application claims priority to German Patent Application Serial No. 10 2013 217 319.9, which was filed Aug. 30, 2013, and is incorporated herein by reference in its entirety.

TECHNICAL FIELD

Various embodiments relate generally to a lighting device.

BACKGROUND

Such a lighting device is disclosed, for example in DE 20 2012 005 157 U1. This document describes a lighting device including a plurality of laser diodes emitting blue light, the light of which is guided onto a light wavelength conversion element by TIR (total internal reflection) optics and a downstream light guide.

SUMMARY

In various embodiments, a lighting device includes at least one laser light source and a light wavelength conversion element. The light wavelength conversion element includes phosphor which is arranged on a surface region of a substrate and is used for wavelength conversion of the light emitted by the at least one laser light source. The light wavelength conversion element has a greater thickness at the edge of the surface region, provided with phosphor, of the substrate than at the surface centroid of the surface region, provided with phosphor, of the substrate. The thickness is respectively measured perpendicularly to the surface region, provided with phosphor, of the substrate.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DESCRIPTION

Figure 1:
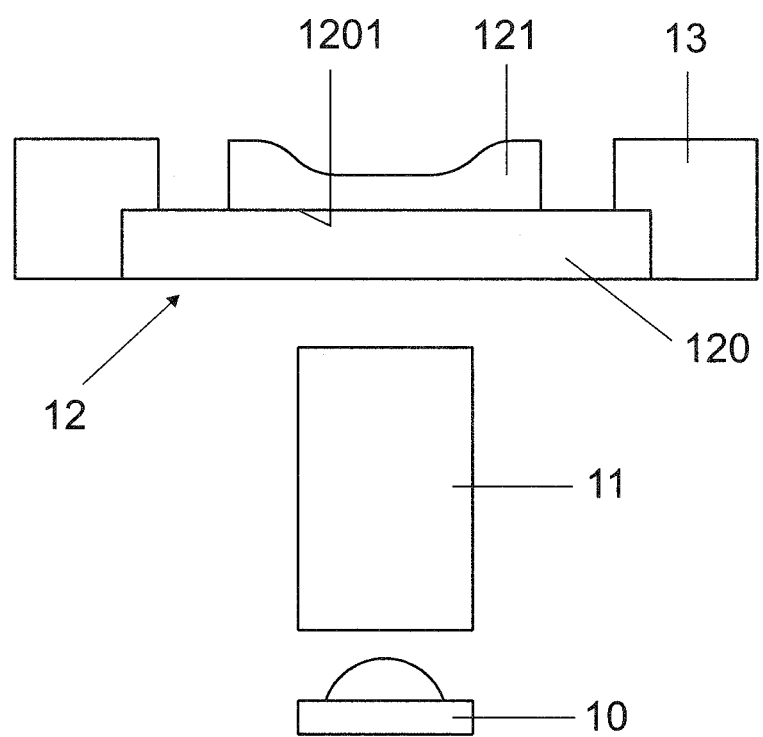
FIG. 1 shows a schematic representation of a lighting device according to various embodiments.

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

The word "over" used with regards to a deposited material formed "over" a side or surface, may be used herein to mean that the deposited material may be formed "directly on", e.g. in direct contact with, the implied side or surface. The word "over" used with regards to a deposited material formed "over" a side or surface, may be used herein to mean that the deposited material may be formed "indirectly on" the implied side or surface with one or more additional layers being arranged between the implied side or surface and the deposited material.

Various embodiments provide a lighting device of the species, the light wavelength conversion element of which is exposed to a lower thermal load during operation of the lighting device.

According to various embodiments, the lighting device has at least one light source, e.g. formed as a laser diode arrangement, and a light wavelength conversion element, the light wavelength conversion element including phosphor which is arranged on a surface region of a substrate and is used for wavelength conversion of the light emitted by the at least one laser light source. According to various embodiments, the light wavelength conversion element has a greater thickness at the edge of the surface region, provided with the phosphor, of the substrate than at the surface centroid of the surface region, provided with phosphor, of the substrate. The thickness is respectively measured perpendicularly to the surface region, provided with phosphor, of the substrate. The term "surface centroid" of the surface region, provided with phosphor, of the substrate refers in the mathematical or physical sense to the surface centroid of the aforementioned surface region. The aforementioned thickness difference of the light wavelength conversion element of the lighting device according to the invention allows better thermal dissipation from the light wavelength conversion element to the surroundings, for example to a cooling body which forms a holder for the light wavelength conversion element, and therefore ensures a reduced thermal load of the light wavelength conversion element during operation of the lighting device according to various embodiments. The at least one laser light source generates, usually by means of downstream optics, a laser beam with an almost homogeneous energy density distribution in the laser beam profile. In this way, when the laser beam is focused onto the surface centroid of the surface region, provided with phosphor, of the substrate, the light wavelength conversion element is heated most strongly by the laser beam at the surface centroid of the aforementioned surface region, since thermal dissipation from this point is more difficult than at the edge of the aforementioned surface region of the substrate. Owing to the Stokes shift which takes place during the wavelength conversion of the laser light, and to conversion losses due to thermal quenching, high power losses are incurred in the light wavelength conversion element, which need to be dissipated from the light wavelength conversion element in the form of heat. For the purpose of better thermal dissipation, according to the various embodiments of the lighting device, the light wavelength conversion element has a greater thickness at the edge of the surface region, provided with phosphor, of the substrate than at the surface centroid of the surface region, provided with phosphor, of the substrate.

In various embodiments, the light wavelength conversion element may include or essentially consist of materials with high thermal conductivity in order to further improve the thermal dissipation and minimize the thermal load of the light wavelength conversion element during operation of the lighting device. In various embodiments, the substrate, provided with phosphor, of the light wavelength conversion element is formed as a sapphire platelet or ceramic platelet, and the phosphor is for example applied on a surface of the substrate by means of adhesive or in the form of a coating. The aforementioned substrate has a particularly high thermal conductivity. The light wavelength conversion element is e.g. fixed on a cooling body or a heat sink, which forms a holder for the light wavelength conversion element, in order to be able to dissipate the heat from the light wavelength conversion element to the surroundings in the most efficient way possible.

The thickness difference in the light wavelength conversion element according to the first embodiment of the lighting device according to the invention may be achieved in various ways.

According to a variant of various embodiments of the lighting device, the phosphor has a greater thickness on the substrate at the edge of the surface region, provided with phosphor, of the substrate than at the surface centroid of the surface region, provided with phosphor, of the substrate. The values of the thickness of the phosphor on the substrate may e.g. lie in the range of from 2 micrometers to 500 micrometers, and e.g. in the value range of 30 micrometers to 300 micrometers. The thickness of the substrate may e.g. lie in the value range of from 0.2 mm to 2 mm.

In various embodiments, the concentration of the wavelength conversion means in the phosphor is reduced according to the increase in the phosphor thickness, in order to avoid as far as possible any change in the relative proportions of converted and unconverted laser light in the light emitted by the lighting device according to various embodiments. Cerium-doped yttrium aluminum garnet (YAG:Ce) may e.g. be used as the phosphor, the concentration of cerium in the yttrium aluminum garnet being reduced according to the increase in the phosphor thickness. In various embodiments, the concentration of cerium in the yttrium aluminum garnet phosphor lies in the value range of from 0.01 to 2 percent by weight, the value of the cerium concentration in the phosphor being less at the edge of the surface region, coated with phosphor, of the substrate than at the surface centroid of the surface region, coated with phosphor, of the substrate. The aforementioned phosphor may e.g. be used in combination with laser light sources emitting blue light, in order to generate white light which is a mixture of unconverted blue light and yellow light converted by means of the aforementioned phosphor.

According to a variant of various embodiments of the lighting device, the substrate has a greater thickness at the edge of its surface region provided with phosphor than at the surface centroid of its surface region provided with phosphor.

This variant may have the effect that the layer thickness of the phosphor and the concentration of the conversion means in the phosphor remain unchanged, and no variation in the proportions of converted and unconverted laser light therefore occurs, so that no influence on the color locus and the color of the light emitted by the lighting device according to various embodiments is caused, the thicker edge of the substrate region provided with phosphor allowing improved thermal dissipation from the light wavelength conversion element. The thickness of the substrate preferably lies in the value range of from 0.2 mm to 2 mm.

The two variants of various embodiments may also be combined with one another. This means that both the thickness of the substrate and the phosphor thickness on the substrate may be varied as described above.

The light wavelength conversion element may e.g. be formed as a disk, the thickness of which increases starting from its center in the direction of its edge. According to various embodiments, the light wavelength conversion element has a circular disk-shaped phosphor element, which may include or essentially consist of cerium-doped yttrium aluminum garnet and is arranged on a substrate, the thickness of the circular disk-shaped phosphor element increasing starting from a minimum value at its middle to a maximum value at its edge, in order to permit good thermal dissipation. The cerium concentration in the phosphor element may e.g. be reduced starting from a maximum value at the middle of the circular disk in the direction of the circular disk edge of the phosphor element to a minimum value at the edge of the circular disk-shaped phosphor element, in order to ensure uniform wavelength conversion of the laser light and light emission with a homogeneous light color over the entire surface of the phosphor element. In various embodiments, the cerium concentration in the phosphor has values in the range of from 0.01 to 2 percent by weight, the value of the cerium concentration in the yttrium aluminum garnet phosphor being less at the edge of the phosphor element than at its middle. The thickness of the circular disk-shaped phosphor element of the lighting device according to various embodiments may e.g. lie in the value range of from 2 micrometers to 500 micrometers, and the thickness of the substrate in the value range of from 0.2 mm to 2 mm.

According to various embodiments, the light wavelength conversion element has a circular disk-shaped phosphor element, which includes or essentially consists of cerium-doped yttrium aluminum garnet and is arranged on a substrate, the substrate being formed as a sapphire or ceramic platelet, and the thickness of the substrate increasing starting from the surface centroid of its surface region provided with phosphor in the direction of the edge of its surface region provided with phosphor, in order to permit good thermal dissipation. These embodiment may have the effect that the cerium concentration may be the same throughout the entire phosphor element, since the thickness of the circular disk-shaped phosphor element does not vary along its radius, and light emission with a homogeneous light color over the entire phosphor element is therefore ensured. The cerium concentration in the yttrium aluminum garnet phosphor of the phosphor element may e.g. lie uniformly at a value in the value range of 0.01 to 2 percent by weight.

According to various embodiments of the lighting device, instead of the thickness of the light wavelength conversion element, the profile of the laser beam directed onto the light wavelength conversion element is varied in such a way that its energy density distribution in a laser spot generated on a surface of the light wavelength conversion element is greater in an edge zone of the laser spot than at the surface centroid of the laser spot. In this way, a homogeneous heat distribution can likewise be achieved over the entire light wavelength conversion element, as well as a reduced thermal load at the middle of the light wavelength conversion element. For example, the laser beam directed onto the light wavelength conversion element may be varied by one or more optical elements before it strikes the light wavelength conversion element, in such a way that its profile has an inhomogeneous energy density distribution instead of a homogeneous energy density distribution, for example an energy density distribution with a donut-like profile.

The technical concepts of the above-described embodiments of the lighting device may also be combined with one another in order to achieve a homogeneous operating temperature, which is as low as possible, at the light wavelength conversion element. This means that both the thickness of the light wavelength conversion element and the laser beam profile may be varied as described above.

FIG. 1 schematically represents the structure of a lighting device according to various embodiments. This lighting device includes a laser diode arrangement 10, optics 11, a light wavelength conversion element 12, and a metal heat sink 13. It is part of a motor vehicle headlamp, which is arranged in the front region of a motor vehicle and is used to generate daytime running light, fog light, position light, high-beam light or low-beam light.

The laser diode arrangement 10 includes at least one laser diode, which emits blue light during its operation. The light emitted by the laser diode arrangement 10 is directed by means of the optics 11, which may be formed as fiber optics, onto the light wavelength conversion element 12. If the laser diode arrangement 10 includes a plurality of laser diodes, then the laser diode arrangement 10 additionally also contains a beam combiner or a similar optical device, which combines the laser beams emitted by the laser diodes to form a single laser beam bundle which is focused onto the light wavelength conversion element 12 by means of the optics 11.

The light wavelength conversion element 12 may include or essentially consist of a circular disk-shaped sapphire platelet 120 and a phosphor element 121, which is arranged on a surface 1201, facing away from the optics 11, of the sapphire platelet 120. The phosphor element 121 is formed as cerium-doped yttrium aluminum garnet ceramic, and is fixed by means of adhesive or in the form of a coating on the surface 1201 of the sapphire platelet 120. The sapphire platelet 120 is transparent, and is used as a substrate for the phosphor element 121. The sapphire platelet 120 is formed as a circular disk with a diameter of 10 mm and a thickness of 0.5 mm, and is fixed in a matching recess of the metal heat sink 13. The phosphor element 121 converts the blue laser radiation emitted by the laser diode arrangement 10 and striking the phosphor element 121 partially into yellow light, so that white light which is a mixture of unconverted blue light and converted yellow light is emitted by the phosphor element 121, or the light wavelength conversion element 12. The relative proportion of unconverted blue light and converted yellow light is determined by the thickness of the phosphor element 121 and the cerium concentration in the phosphor element 121.

The phosphor element 121 is formed in the shape of a circular disk, is arranged coaxially with the rotational symmetry axis of the sapphire platelet 12 and has a diameter of 2 mm. The thickness D, measured perpendicularly to the disk plane, of the circular disk-shaped phosphor element 121 varies along its radius. At the middle of the circular disk-shaped phosphor element 121, it has a minimum value of 2 micrometers, and at the edge it has a maximum value of 500 micrometers. The cerium concentration in the yttrium aluminum garnet is substantially higher at the middle of the phosphor element 121 than at the edge of the phosphor element 121. The actual values of the cerium concentration at the edge and at the middle of the phosphor element 121 also additionally depend on the desired color temperature of the white mixed light. They lie in the value range of from 0.01 to 2 percent by weight, higher values of the cerium concentration in the phosphor being selected for white light with a high color temperature than for white light with a low color temperature.

Figure 4:
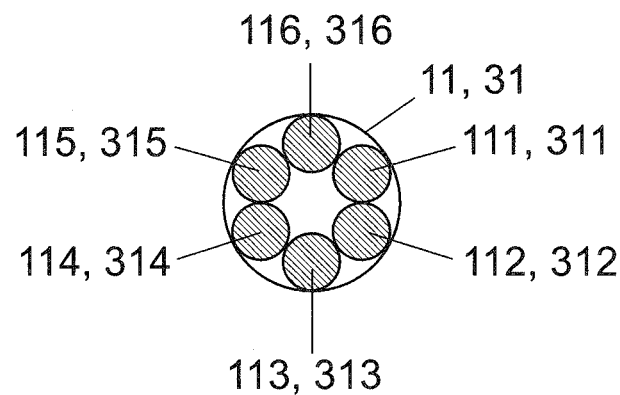
FIG. 4 shows a cross section through the optics of the lighting devices depicted in FIG. 1 and FIG. 3.
Figure 6:
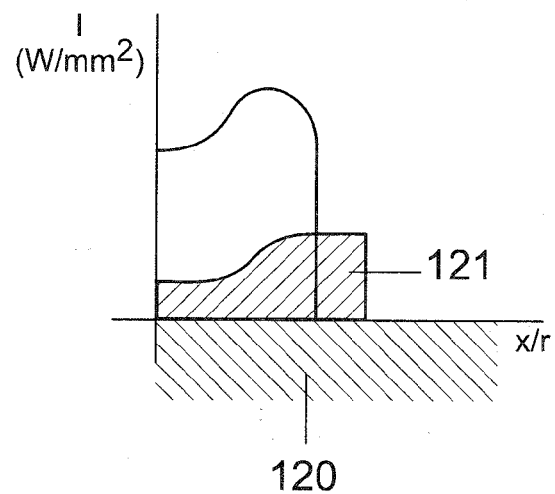
FIGS. 6A to 6C show a schematic representation of the energy density distribution in the profile of the laser beam directed onto the phosphor, and of the temperature distribution in the phosphor, for a laser beam profile with a reduced energy density in the middle of the laser beam, as well as the cerium concentration in the phosphor, for various embodiments depicted in FIG. 1.
Figure 6:
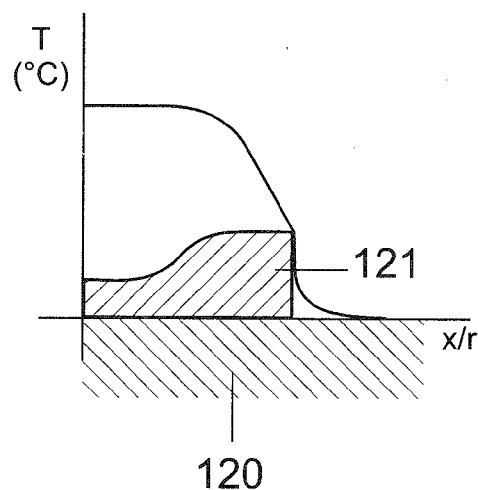
Figure 6:
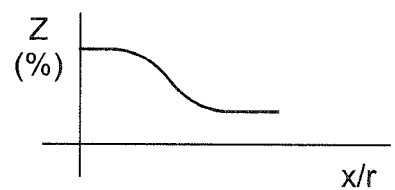

By means of the fiber optics 11, the laser beam bundle is directed onto the light wavelength conversion element 12 in such a way that a large part of the surface, facing toward the sapphire platelet 120, of the phosphor element 121 is illuminated by the laser beam bundle. The laser spot generated on the sapphire platelet 120, or on the phosphor element 121, has a diameter of 0.6 mm. The laser spot is placed centrally on the sapphire platelet 120 and the phosphor element 121. FIG. 4 schematically represents a cross section through the fiber optics 11. The fiber optics 11 includes a plurality of fibers 111, 112, 113, 114, 115, 116, which are arranged in cross section around a ring. Light is launched into each fiber by means of at least one laser diode of the laser diode arrangement 10. In this way, a donut-like energy density distribution, which is depicted schematically and qualitatively in the first diagram in FIG. 6A is imparted to the laser beam bundle emitted by the laser diode arrangement 10 after the laser beam bundle leaves the fiber optics 11. The energy density I of the laser beam bundle is much less at the middle of the laser spot, generated by the laser beam bundle, on the sapphire platelet 120, or phosphor element 121, than at the edge of the laser spot, so that the thin central region of the phosphor element 121 is exposed to a lower laser energy than the thicker edge region of the phosphor element 121. In the first diagram of FIG. 6A, the energy density I of the laser beam bundle striking the phosphor element 121 is depicted schematically and in arbitrary units as a function of the distance x from the rotational symmetry axis of the circular disk-shaped phosphor element 121. On the horizontal axis in all three diagrams of FIG. 6A, FIG. 6B and FIG. 6C, the ratio of the aforementioned distance x and the radius r of the phosphor element 121 is plotted. Owing to this energy density distribution I in the profile of the laser beam bundle, an almost homogeneous temperature T is established in the phosphor element 121. In the second diagram of FIG. 6B, the temperature profile T in the phosphor element 121, that is to say the temperature as a function of the distance x from the rotational symmetry axis of the circular disk-shape phosphor element 121, is depicted schematically and qualitatively, and in arbitrary units. The third diagram of FIG. 6C shows schematically and only qualitatively the concentration Z of cerium in the phosphor element 121 as a function of the distance x from the rotational symmetry axis of the circular disk-shaped phosphor element 121. The concentration of cerium is greatest at the center of the phosphor element 121 and decreases in the direction toward its edge, in order to ensure homogeneous wavelength conversion with almost identical relative proportions of converted and unconverted laser light over the entire phosphor element.

Figure 2:
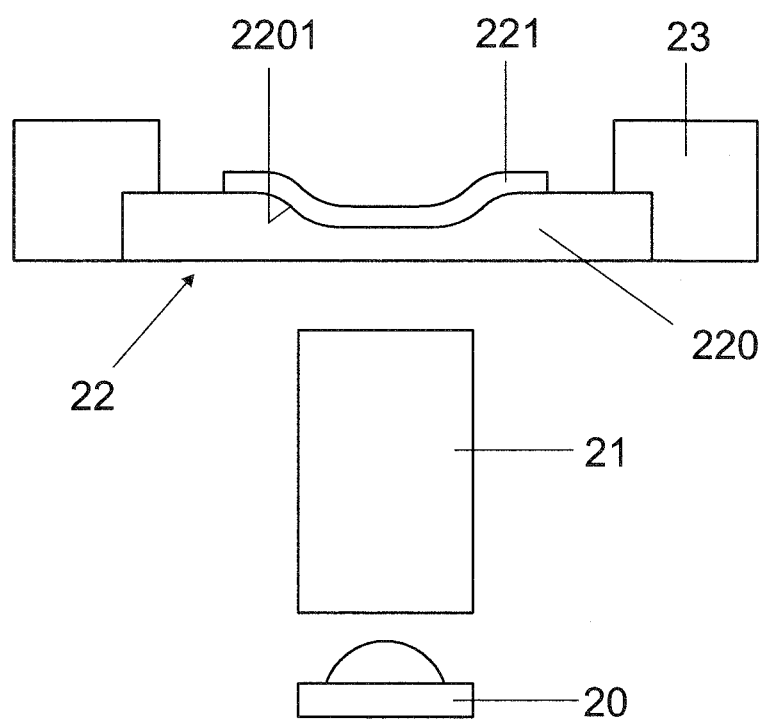
FIG. 2 shows a schematic representation of a lighting device according to various embodiments.

FIG. 2 schematically represents the structure of a lighting device according to various embodiments. This lighting device has a laser diode arrangement 20, optics 21, a light wavelength conversion element 22 and a metal heat sink 23. It is part of a motor vehicle headlamp, which is arranged in the front region of a motor vehicle and is used to generate daytime running light, fog light, position light, high-beam light or low-beam light.

The laser diode arrangement 20 includes at least one laser diode, which emits blue light during its operation. The light emitted by the laser diode arrangement 20 is focused by means of the optics 21, which may be formed as fiber optics, onto the light wavelength conversion element 22. If the laser diode arrangement 20 includes a plurality of laser diodes, then the laser diode arrangement 20 additionally also contains a beam combiner or a similar optical device, which combines the laser beams emitted by the laser diodes to form a single laser beam bundle which is directed onto the light wavelength conversion element 22 by means of the optics 21.

The light wavelength conversion element 22 may include or essentially consist of a circular disk-shaped sapphire platelet 220 and a phosphor element 221, which is arranged on a surface 2201, facing away from the optics 21, of the sapphire platelet 220. The phosphor element 221 is formed as cerium-doped yttrium aluminum garnet, and is fixed by means of adhesive or in the form of a coating on the surface 2201 of the sapphire platelet 220. The sapphire platelet 220 is transparent, and is used as a substrate for the phosphor element 221. The sapphire platelet 220 is formed as a circular disk with a diameter of 10 mm, and is fixed in a matching recess of the metal heat sink 23. The thickness of the sapphire platelet 220, measured perpendicularly to the disk plane, varies along its radius. It has a value of 0.5 mm at the middle of the circular disk-shaped sapphire platelet 220 and a value of 1 mm at the edge.

The phosphor element 221 converts the blue laser radiation emitted by the laser diode arrangement 20 and striking the phosphor element 221 partially into yellow light, so that white light which is a mixture of unconverted blue light and converted yellow light is emitted by the phosphor element 221, or the light wavelength conversion element 22. The relative proportion of unconverted blue light and converted yellow light is determined by the thickness of the phosphor element 221 and the cerium concentration in the phosphor element 221.

The phosphor element 221 is formed as a circular disk-shaped coating, is arranged coaxially with the rotational symmetry axis of the sapphire platelet 220 on the surface 2201 of the sapphire platelet 220, and has a diameter of 2 mm and a uniform layer thickness of 100 micrometers. The cerium concentration in the yttrium aluminum garnet of the phosphor element 221 is homogeneous and has a value in the value range of from 0.01 to 2 percent by weight.

By means of the fiber optics 21, the laser beam bundle is directed onto the light wavelength conversion element 22 in such a way that a large part of the surface, facing toward the sapphire platelet 220, of the phosphor element 221 is illuminated by the laser beam bundle. The laser spot generated on the sapphire platelet 220, or on the phosphor element 221, has a diameter of 0.6 mm. The laser spot is placed centrally on the sapphire platelet 220 and the phosphor element 221. The laser beam bundle emitted by the laser diode arrangement 20 and directed by the fiber optics 21 onto the light wavelength conversion element 22, has an almost homogeneous energy density distribution. The temperature profile in the phosphor element 221 is similar to the temperature profile of the phosphor element 121 as represented in the second diagram of FIG. 6B.

Figure 3:
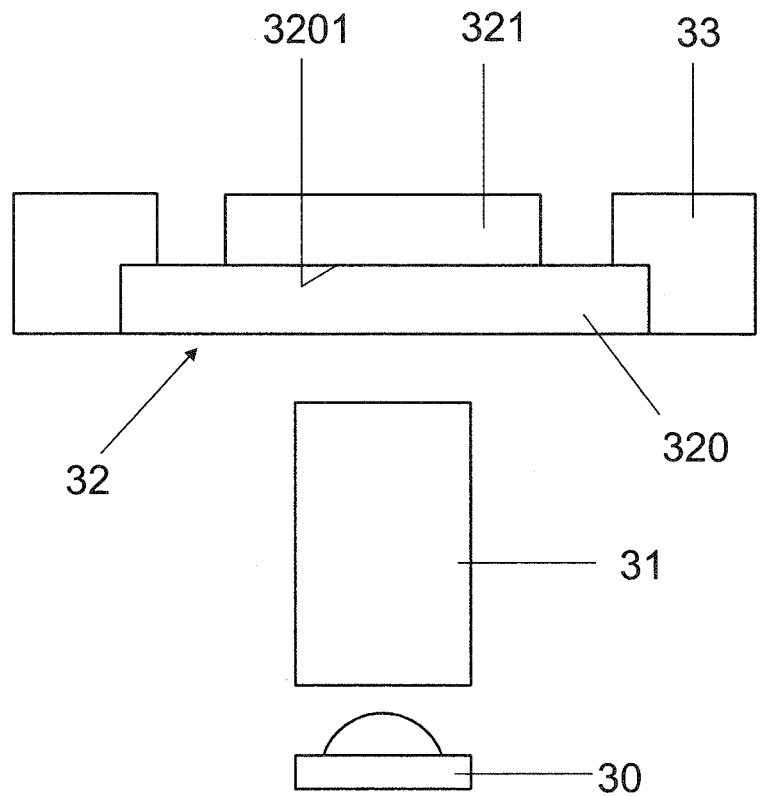
FIG. 3 shows a schematic representation of a lighting device according to various embodiments.

FIG. 3 schematically represents the structure of a lighting device according to various embodiments. This lighting device has a laser diode arrangement 30, optics 31, a light wavelength conversion element 32 and a metal heat sink 33. It is part of a motor vehicle headlamp, which is arranged in the front region of a motor vehicle and is used to generate daytime running light, fog light, position light, high-beam light or low-beam light.

The laser diode arrangement 30 includes at least one laser diode, which emits blue light during its operation. The light emitted by the laser diode arrangement 30 is focused by means of the optics 31, which may be formed as fiber optics, onto the light wavelength conversion element 32. If the laser diode arrangement 30 includes a plurality of laser diodes, then the laser diode arrangement 30 additionally also contains a beam combiner or a similar optical device, which combines the laser beams emitted by the laser diodes to form a single laser beam bundle which is directed onto the light wavelength conversion element 32 by means of the optics 31.

The light wavelength conversion element 32 may include or essentially consist of a circular disk-shaped sapphire platelet 320 and a phosphor element 321, which is arranged on a surface 3201, facing away from the optics 31, of the sapphire platelet 320. The phosphor element 321 is formed as cerium-doped yttrium aluminum garnet ceramic, and is fixed by means of adhesive or in the form of a coating on the surface 3201 of the sapphire platelet 320. The sapphire platelet 320 is transparent, and is used as a substrate for the phosphor element 321. The sapphire platelet 320 is formed as a circular disk with a diameter of 10 mm and a thickness of 0.5 mm, and is fixed in a matching recess of the metal heat sink 33. The phosphor element 321 converts the blue laser radiation emitted by the laser diode arrangement 30 and striking the phosphor element 321 partially into yellow light, so that white light which is a mixture of unconverted blue light and converted yellow light is emitted by the phosphor element 321, or the light wavelength conversion element 32. The relative proportion of unconverted blue light and converted yellow light is determined by the thickness of the phosphor element 321 and the cerium concentration in the phosphor element 321.

The phosphor element 321 is formed in the shape of a circular disk, is arranged coaxially with the rotational symmetry axis of the sapphire platelet 320 and has a diameter of 2 mm. The thickness D of the circular disk-shaped phosphor element 321, measured perpendicularly to the disk plane, is uniformly 100 micrometers. The cerium concentration in the yttrium aluminum garnet phosphor is homogeneous throughout the entire phosphor element 321, and has a value in the value range of from 0.01 to 2 percent by weight, expressed in terms of the total weight of the phosphor element. The value of the cerium concentration in the yttrium aluminum garnet phosphor depends on the desired color temperature of the white mixed light.

Figure 5A:
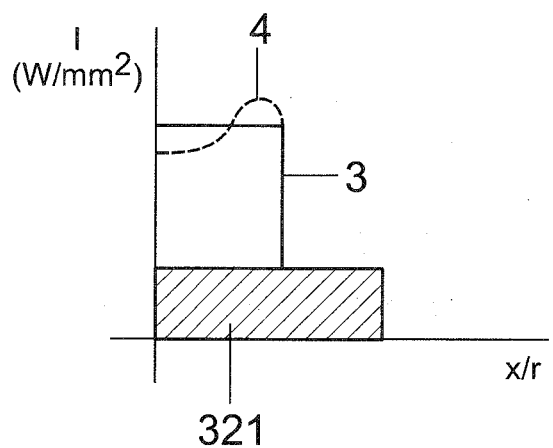
FIGS. 5A and 5B show a schematic representation of the energy density distribution in the profile of the laser beam directed onto the phosphor, and of the temperature distribution in the phosphor, respectively for a laser beam profile with a homogeneous energy density distribution and an energy density distribution according to various embodiments depicted in FIG. 3.
Figure 5B:
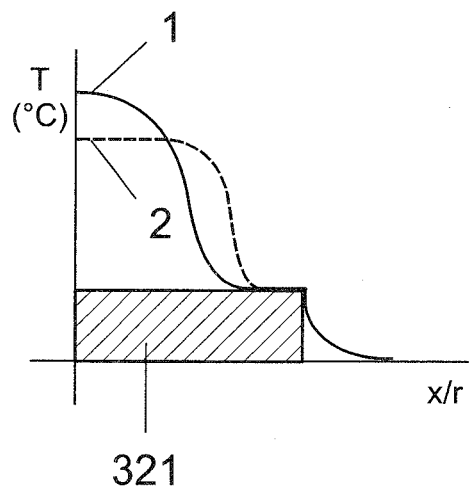

By means of the fiber optics 31, the laser beam bundle is directed onto the light wavelength conversion element 32 in such a way that a large part of the surface, facing toward the sapphire platelet 320, of the phosphor element 321 is illuminated by the laser beam bundle. The laser spot generated on the sapphire platelet 320, or on the phosphor element 321, has a diameter of 0.6 mm. The laser spot is placed centrally on the sapphire platelet 320 and the phosphor element 321. FIG. 4 schematically represents a cross section through the fiber optics 31. The fiber optics 31 includes a plurality of fibers 311, 312, 313, 314, 315, 316, which are arranged in cross section around a ring. Light is launched into each fiber by means of at least one laser diode of the laser diode arrangement 30. In this way, a donut-like energy density distribution, which is represented schematically and qualitatively in the first diagram in FIG. 5A by the curve 4 with a dashed line, is imparted to the laser beam bundle emitted by the laser diode arrangement 30 after the laser beam bundle leaves the fiber optics 31. The energy density I of the laser beam bundle is much less at the middle of the laser spot, generated by the laser beam bundle, on the sapphire platelet 320, or phosphor element 321, than at annular edge zone of the laser spot, so that the central region of the phosphor element 321 is exposed to a lower laser energy than the edge region of the phosphor element 321. In the first diagram of FIG. 5A, the energy density I of the laser beam bundle striking the phosphor element 321 is depicted schematically and in arbitrary units as a function of the distance x from the rotational symmetry axis of the circular disk-shaped phosphor element 321. In both diagrams of FIGS. 5A and 5B, the ratio of the aforementioned distance x and the radius r of the phosphor element 321 is plotted on the horizontal axis. The dashed line 4 shows the energy density distribution I in the case of the lighting device according to the various embodiments, and the solid line 3 shows for comparison a laser beam bundle with a homogeneous energy density distribution I.

Owing to this inhomogeneous energy density distribution in the profile of the laser beam bundle, an almost homogeneous temperature T is established in the phosphor element 321. In the second diagram of FIG. 5B, the temperature profile T in the phosphor element 321, that is to say the temperature T as a function of the distance from the rotational symmetry axis of the circular disk-shaped phosphor element 321, is depicted schematically and qualitatively, and in arbitrary units. The curve 2 represented by a dashed line shows the temperature profile T for the inhomogeneous energy density distribution in the laser beam bundle according to various embodiments of the lighting device, while the curve 1 plotted with a solid line shows the temperature profile T in the phosphor element 321 for a homogeneous energy density distribution I in the laser beam bundle.

The various embodiments are not restricted to the embodiments which have been explained in detail above. For example, the technical effects of the various embodiments, that is to say the variation of the thickness of the phosphor element and of the substrate, as well as the inhomogeneous energy density distribution of the laser beam bundle, may respectively be provided individually or in combination. Furthermore, other laser light sources or various laser light sources of different wavelength (UV, visible, IR) may be used or combined with one another. Furthermore, other or several phosphors may be used. Furthermore, for example, a ceramic platelet may also be used instead of a sapphire platelet as substrate for the phosphor element or the phosphor. The substrate and the phosphor element may have any desired shapes, for example rectangular or polygonal. The embodiments may be used not only for transmissive arrangements, but also for reflective arrangements, in which unconverted laser excitation radiation and conversion light is emitted in the direction of the laser incidence direction.

Other fields of application of various embodiments are for example in the field of video and data projection, in endoscopy lighting, as microscope lighting, as a light source for operating theater lighting and other medical lighting applications in therapy and diagnosis as well as in the field of general lighting, and street lighting.

The thickness variation of the phosphor or of the substrate may take place continuously, according to any desired curve shape. The curve shapes of the energy density of the laser beam bundle and the curve shapes of the thickness variation of the phosphor element or of the substrate may also be formed complementarily. This means that an increase in the thickness of the phosphor element of the substrate, starting from the rotational symmetry axis of the phosphor element in the direction of its edge, is correlated with a decrease of the energy density of the laser beam bundle.

As an alternative or in addition, the thickness variation of the phosphor or of the substrate may also take place in stages.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A lighting device, comprising:
   at least one laser light source; and
   a light wavelength conversion element;
   the light wavelength conversion element comprising phosphor which is arranged on a surface region of a substrate and is used for wavelength conversion of the light emitted by the at least one laser light source;
   wherein the light wavelength conversion element has a greater thickness at the edge of the surface region, provided with phosphor, of the substrate than at the surface centroid of the surface region, provided with phosphor, of the substrate, the thickness respectively being measured perpendicularly to the surface region, provided with phosphor, of the substrate,
   wherein the phosphor has a greater thickness on the substrate at the edge of the surface region, provided with phosphor, of the substrate than at the surface centroid of the surface region, provided with phosphor, of the substrate, and
   wherein the concentration of a wavelength conversion means in the phosphor is less at the edge of the surface region, provided with phosphor, of the substrate than at the surface centroid of the surface region, provided with phosphor, of the substrate.

2. The lighting device of claim 1,
   wherein the substrate provided with phosphor has a greater thickness at the edge of the surface region provided with phosphor than at the surface centroid of the surface region, provided with phosphor, of the substrate.

3. The lighting device of claim 1,
   wherein the thickness of the phosphor lies in the range from 2 micrometers to 500 micrometers.

4. The lighting device of claim 1,
   wherein the substrate is formed as a sapphire or ceramic platelet.

5. The lighting device of claim 1,
   which is formed in such a way that a laser beam directed onto the light wavelength conversion element is generated with a laser spot on a surface of the light wavelength conversion element, the energy density of the laser beam being greater in an edge zone of the laser spot than at the surface centroid of the laser spot.

* * * * *